United States Patent [19]

Perlman

[11] Patent Number: 4,859,423
[45] Date of Patent: Aug. 22, 1989

[54] PLASTIC PIPETTE CANISTER

[75] Inventor: Daniel Perlman, Arlington, Mass.

[73] Assignee: Brandeis University, Waltham, Mass.

[21] Appl. No.: 130,397

[22] Filed: Dec. 9, 1987

[51] Int. Cl.⁴ .................... B65D 85/20; B65D 85/30; B65D 85/38; B65D 85/40
[52] U.S. Cl. .................................. 422/102; 422/299; 422/300; 422/307; 422/310; 436/1; 206/214; 206/305; 206/419; 206/443; 206/524.1; 206/524.6; 206/586
[58] Field of Search .................. 422/26, 28, 102, 297, 422/300, 307, 310; 436/1; 206/214, 305, 419, 443, 524.1, 524.6, 586; 220/82 R, 85 A

[56] References Cited

U.S. PATENT DOCUMENTS

| | | | |
|---|---|---|---|
| 2,614,027 | 10/1952 | Kollsman | 21/96 |
| 3,474,929 | 10/1969 | Harker | 220/19 |
| 4,046,254 | 9/1977 | Kramer | 422/26 X |
| 4,191,291 | 3/1980 | Brown | 206/369 |
| 4,349,118 | 9/1982 | Sanderson et al. | 422/26 X |
| 4,436,700 | 3/1984 | Erickson | 422/102 |
| 4,466,552 | 8/1984 | Butterworth et al. | 220/354 |
| 4,541,992 | 9/1985 | Jerge et al. | 422/300 |
| 4,643,303 | 2/1987 | Arp et al. | 207/370 |
| 4,661,326 | 4/1987 | Schainholz | 422/310 |

*Primary Examiner*—Benoit Castel
*Assistant Examiner*—Lynn Kummert

[57] ABSTRACT

A pipette canister formed from a thermoplastic material. The canister withstands dry heat above 160° C. reduces breakage of glass pipettes stored within, and the material is free from metal oxide residues.

6 Claims, 1 Drawing Sheet

PLASTIC PIPETTE CANISTER

BACKGROUND OF THE INVENTION

This invention relates to canisters suitable for holding glass pipettes for sterilization.

Glass pipettes are commonly used for accurately measuring and dispensing volumes of fluids. For some uses it is important to dispense such fluids in a sterile manner and thus the pipettes are sterilized either by dry heat at 160°-180° C. or by steam heat at 121° C. in an autoclave. During sterilization, and subsequent storage, groups of pipettes are held within a cylindrical or rectangular box-shaped canister having a lid. These canisters are commonly formed from stainless steel or aluminum, and are provided with a wad of cotton or glass wool to cushion the fragile tips of pipettes, which otherwise break upon impact with the bottom of the canister during loading or transport of the canisters.

Harker, U.S. Pat. No. 3,474,929, describes an open wire container having a plastic bag containing disinfectant. The bag is autoclaved when filled with pipettes. After use this bag is thrown away.

Erickson, U.S. Pat. No. 4,436,700, describes a stainless steel canister having a flat disc-shaped bottom, suitable for autoclaving of pipettes.

SUMMARY OF THE INVENTION

The invention features a canister for housing and sterilizing glass pipettes. The canister is formed from a thermoplastic material. The canister withstands steam heat above 120° C. and dry heat above 160° C., and the thermoplastic material is chemically inert and free of contaminating metal oxide residues. Further, the plastic reduces the possibility of breakage of glass pipettes upon impact with the canister.

In preferred embodiments, the material is optically transparent, has a thickness of 1/16" or more, and is polyetherimide, polysulfone, or other suitable heat-stable thermoplastic extruded as a cylinder or rectangular canister. The pipette canister has a base formed at an acute angle to the longitudinal axis of the canister, wherein the base causes pipettes inserted into the canister and in contact with the base to be offset from one another, and wherein any one pipette can be removed from the canister without the hand of a person removing the pipette touching other pipettes; the pipette canister has an aperture near its top end, the aperture being narrower than the internal diameter along the length of the canister, wherein an individual pipette can pass through the aperture and be delivered to a user in a sterile condition.

This invention provides a pipette canister which allows sterilization of glass pipettes without compromising their chemical cleanliness or physical integrity. Unlike metal canisters, the present thermoplastic canister avoids transfer of metal ions or metal compounds to the pipettes during sterilization or storage. Thus the sterile pipettes are suitable for use in experiments in which trace metal elements or metal oxides affect the outcome of the experiment. A highly desirable feature and advantage over metal canisters is the breakage protection afforded glass pipettes housed in plastic canisters. This protection appears to derive from both the flexibility and relative softness of the plastic surfaces compared to metal surfaces. Further, since the canister is transparent, and remains so even after several uses, visual inspection of the inner portion of the canister is possible and any visible residues remaining after use can be readily removed. Thus, these residues are not transferred in future use to other pipettes. This transparency also provides visual inspection of the type, size, number, and integrity of pipettes within a canister. In addition, the canister can be formed with a flexible plastic base, suitable for causing each pipette in the canister to be offset from each other with their mouthpieces fanned out at different distances from the lip of the canister. Thus, a single pipette can be removed from the canister without affecting the sterility of other pipettes. Similarly, a funnel-shaped exit port can be formed at the open end of the canister and allow pipettes to be individually delivered from the canister. Flexibility of the various plastic surfaces inside the canister eliminates the need for cushions e.g., glass wool, in protecting the ends of pipettes from breakage. Solid glass, if used to fabricate such a pipette canister, would confer some of the above advantages over metal, but would create a fragile container, itself susceptible to breakage, and contribute to breakage of the pipettes within.

Other features and advantages of the invention will be apparent from the following description of the preferred embodiments, and from the claims.

DESCRIPTION OF THE PREFERRED EMBODIMENTS

Figure 1:
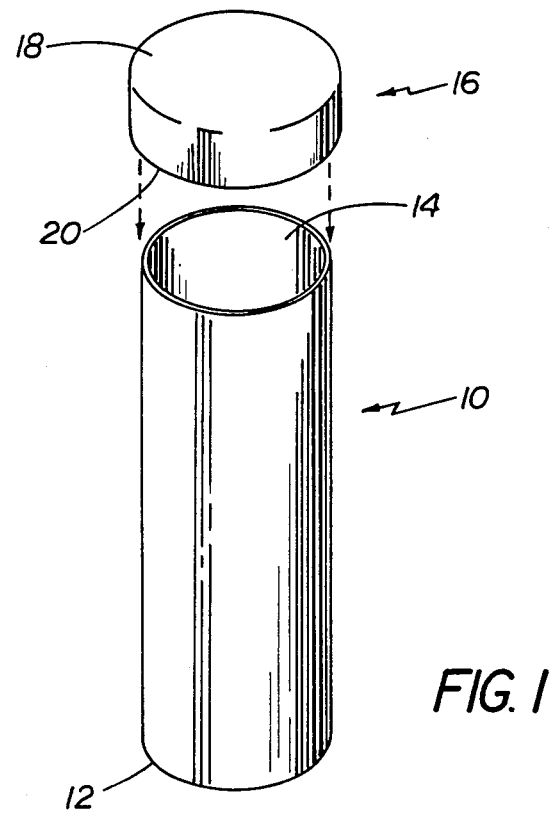
Figure 2:
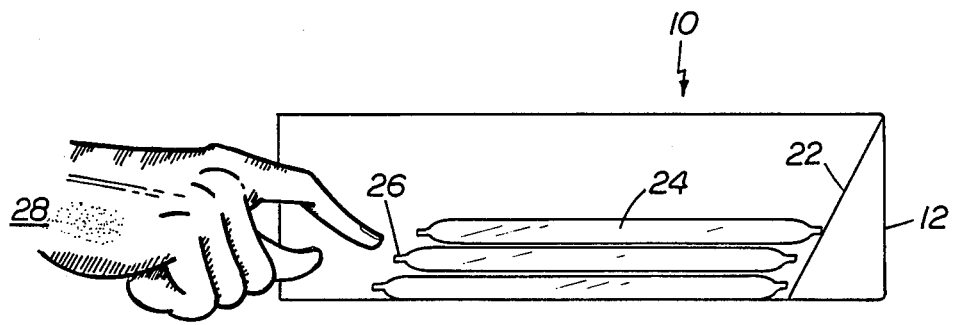
Figure 3:
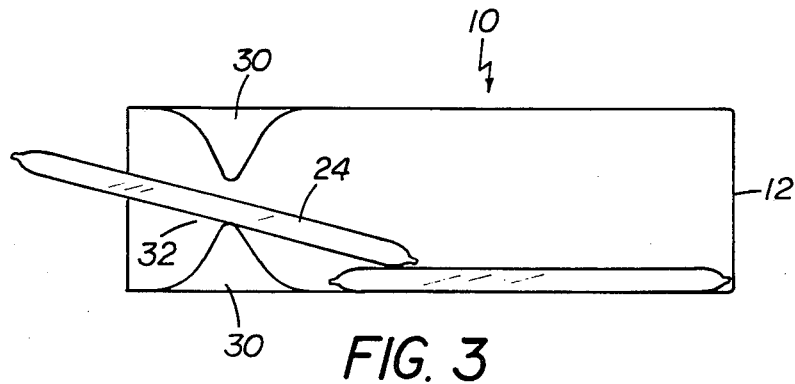

The Figures will first be briefly described. Drawings
FIG. 1 is a perspective view of a canister and its cap;
FIG. 2 is a longitudinal sectional view of a canister having a slanted base; and
FIG. 3 is a longitudinal sectional view of a canister having a funnel shaped exit port.

STRUCTURE

Referring to FIG. 1, canister 10 is generally an elongated cylinder formed of extruded polyetherimide (Ultem ™, manufactured by General Electric). Canister 10 has a circular base 12, an open end 14 and a wall thickness about 1/16". Also provided is a cap 16, which is a cylinder having a base 18 and an opening 20, sized to slide over the open end 14 of canister 10.

Referring to FIG. 2, in one embodiment canister 10 is provided with a removable sloping plastic surface 22 at its base. Surface 22 acts to cause pipettes 24 within canister 10 to fan out so that each mouthpiece 26 is separated and separably accessible to a hand 28 of a person. Surface 22 is also formed from polyetherimide and is inclined at an angle of about 30° to base 12.

Referring to FIG. 3, in another embodiment canister 10 is provided with a removable funnel shaped exit port 30 formed of polyetherimide. Port 30 has an opening 32, wide enough to allow passage of at least one pipette 24.

Use

Canister 10 is used in a standard way by inserting pipettes 24 to be sterilized within the canister inserting port 30 when required and placing lid 16 over opening 14 and placing canister 10 within an oven or within an autoclave. It is preferred that sterilization is by dry heat since steam borne aerosol material in an autoclave may cause chemical contamination of the pipettes.

Other embodiments are within the following claims.

I claim:

1. A pipette canister comprising an elongated tube having a longitudinal axis along a length of said tube, said axis having an internal length greater than the length of a pipette, and having a diameter sufficient to allow storage of a plurality of pipettes, said tube having a closed base and an open top end wherein said canister is formed from a thermoplastic material consisting essentially of polyetherimide, said canister can withstand steam heat above 120° C., and dry heat above 160° C., said material is free from metal oxide residues, and wherein glass pipettes are protected from impact-breakage with said canister by the use of said thermoplastic material.

2. The pipette canister of claim 1 wherein said material is optically transparent.

3. The pipette canister of claim 1, having a wall thickness of 1/16" or more.

4. The pipette canister of claim 1, wherein said material is extruded as a cylindrical or rectangular cross-section.

5. The pipette canister of claim 1, having the closed base formed at an acute angle to the longitudinal axis of said canister, wherein said base causes pipettes inserted into said canister and in contact with said base to be offset from one another, each pipette having a mouthpiece, wherein each mouthpiece can be separately grasped, thereby enabling removal of a pipette canister without touching a mouthpiece of other pipettes.

6. The pipette canister of claim 1, said canister having a known diameter and having means defining an aperture near said top end, said aperture being narrower than the diameter of said canister along the length of said canister, wherein an individual pipette can pass through said aperture and be delivered to a user in a sterile condition.

* * * * *